United States Patent
Pananen

(10) Patent No.: US 9,731,067 B2
(45) Date of Patent: Aug. 15, 2017

(54) MECHANICAL INJECTION PUMP AND METHOD OF USE

(71) Applicant: MEDTRONIC MINIMED, INC., Northridge, CA (US)

(72) Inventor: Jacob E. Pananen, Santa Monica, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 241 days.

(21) Appl. No.: 14/553,584

(22) Filed: Nov. 25, 2014

(65) Prior Publication Data
US 2016/0144101 A1     May 26, 2016

(51) Int. Cl.
*A61M 5/14*     (2006.01)
*A61M 5/145*     (2006.01)
(Continued)

(52) U.S. Cl.
CPC ........ *A61M 5/1408* (2013.01); *A61M 5/1409* (2013.01); *A61M 5/1452* (2013.01); *A61M 5/14248* (2013.01); *A61M 5/148* (2013.01); *A61M 2005/2433* (2013.01); *A61M 2005/2474* (2013.01); *A61M 2205/582* (2013.01); *A61M 2205/6045* (2013.01)

(58) Field of Classification Search
CPC .......... A61M 5/14244; A61M 5/16831; A61M 2209/045; A61M 5/14566; A61M 5/16827; A61M 5/1407; A61M 5/1408
See application file for complete search history.

(56) References Cited

U.S. PATENT DOCUMENTS

| 4,755,173 A | | 7/1988 | Konopka et al. |
| 5,329,976 A | * | 7/1994 | Haber .................. A61J 1/2089 141/18 |

(Continued)

FOREIGN PATENT DOCUMENTS

| WO | 2007108987 A2 | 9/2007 |
| WO | 2007108987 A3 | 9/2007 |

OTHER PUBLICATIONS

Notification of Transmittal of the International Search Report and the Written Opinion of the International Searching Authority, or the Declaration dated Mar. 7, 2016 for Application No. PCT/US2015/062179.

*Primary Examiner* — Bradley Osinski
(74) *Attorney, Agent, or Firm* — Medtronic MiniMed, Inc.

(57) ABSTRACT

A mechanical injection pump wearable by a user to deliver a first fluid and a second fluid, including: a pump body having a first fluid chamber to hold the first fluid and a second fluid chamber to hold the second fluid; a common connector having a first inlet, a second inlet, and a common outlet; a first fluid system including the first fluid chamber, a first button drive connected to the first fluid chamber, and first fluid delivery path between the first fluid chamber and the first inlet; and a second fluid system including the second fluid chamber, a second button drive connected to the second fluid chamber, and second fluid delivery path between the second fluid chamber and the second inlet. Force by the user on the button drive increases pressure within the fluid chamber to drive a predetermined volume of the fluid from the fluid chamber.

14 Claims, 5 Drawing Sheets

(51) Int. Cl.
*A61M 5/142* (2006.01)
*A61M 5/148* (2006.01)
*A61M 5/24* (2006.01)

(56) References Cited

U.S. PATENT DOCUMENTS

| | | | |
|---|---|---|---|
| 5,391,250 A | 2/1995 | Cheney, II et al. |
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2007/0088271 A1* | 4/2007 | Richards ............ A61M 5/14244 |
| | | 604/151 |
| 2007/0123819 A1 | 5/2007 | Mernoe et al. |
| 2007/0299398 A1* | 12/2007 | Alferness .......... A61M 5/14248 |
| | | 604/151 |
| 2010/0160861 A1 | 6/2010 | Causey, III et al. |
| 2011/0319861 A1 | 12/2011 | Wilk |

\* cited by examiner

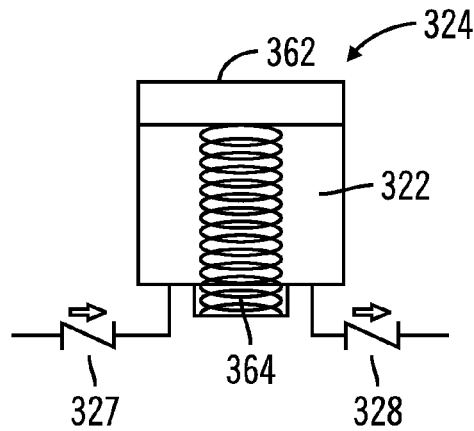
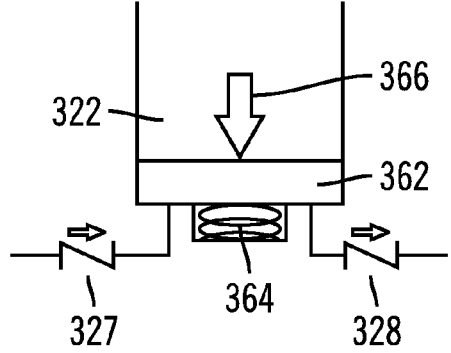
FIG. 3A  FIG. 3B
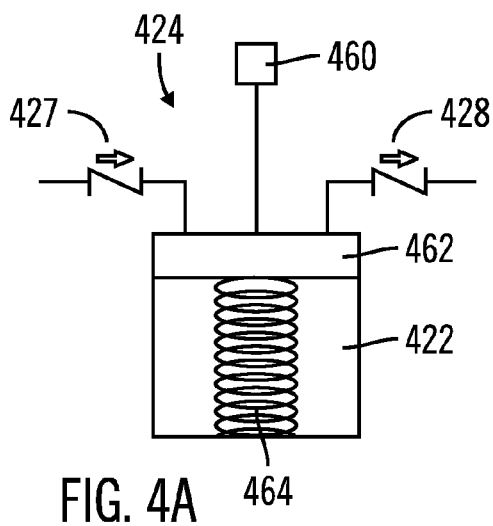
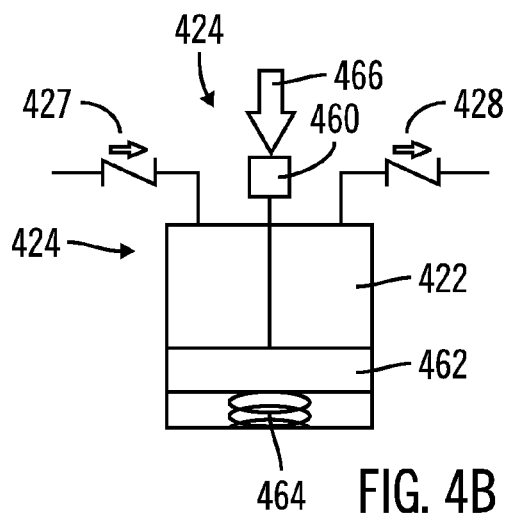
FIG. 4A  FIG. 4B
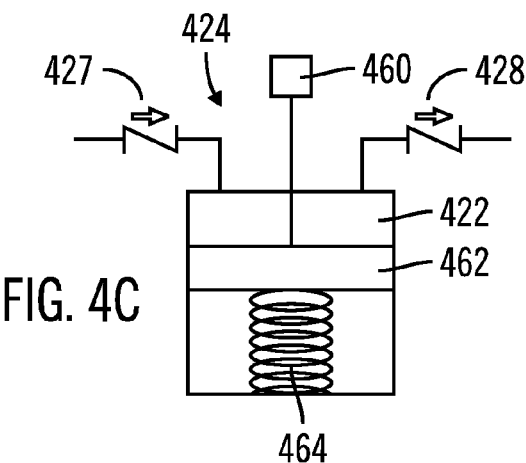
FIG. 4C

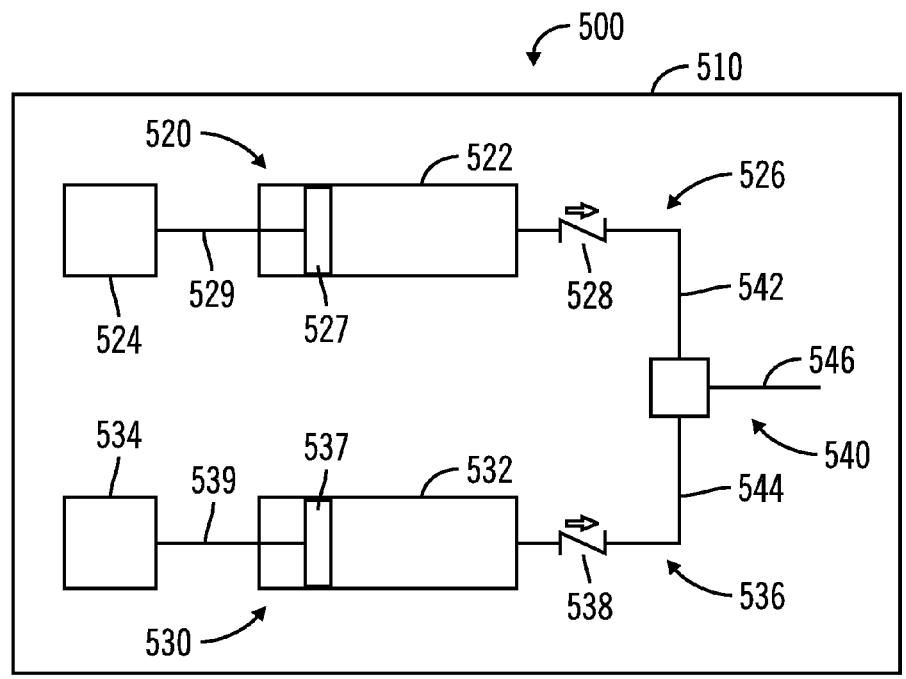
FIG. 5
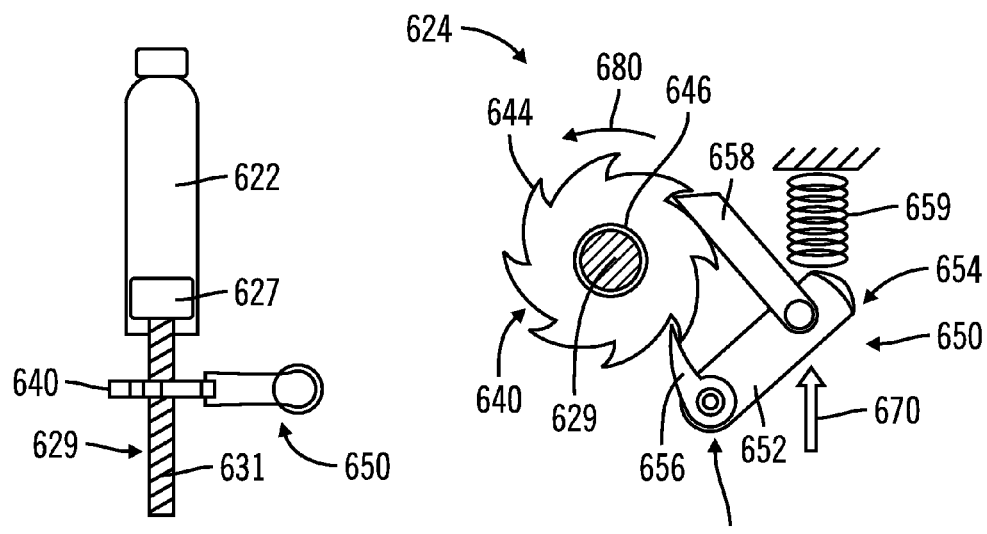
FIG. 6A
FIG. 6B

MECHANICAL INJECTION PUMP AND METHOD OF USE

TECHNICAL FIELD

The technical field of this disclosure is personal medical systems, particularly, mechanical injection pumps and methods of use.

BACKGROUND OF THE INVENTION

Certain medical conditions or diseases require that patients intermittently inject a drug or therapeutic agent subcutaneously to maintain the medical condition or disease under control. Multiple daily injections (MDIs) may be required. One such medical condition is diabetes, for which insulin is injected to regulate blood glucose. An estimated twenty-six million people in the United States, or about 8% of the population, have diabetes. This percentage is expected to increase in the near-term as the population ages.

To achieve better control over blood sugar levels, basal-bolus therapy is often recommended for people with Type 1 or Type 2 diabetes. Basal-bolus insulin therapy is delivered either through multiple daily injections (MDIs) or through insulin pump therapy. The goal of basal-bolus therapy is to mimic the way blood sugar is controlled naturally.

Multiple daily injections use an insulin pen or a syringe and require the use of two different insulin types for bolus and basal therapy. Long acting insulin, or basal insulin, begins working in 1-2 hours but is slowly released so it can last up to 24 hours to keep blood glucose levels at consistent levels during periods of fasting. Rapid acting insulin, or bolus insulin, is specifically taken at meal times to keep blood sugar levels under control following a meal.

Insulin pump therapy uses an insulin pump and requires only a single type of insulin (usually rapid acting) that is delivered during a meal as a bolus injection, and slowly and continuously throughout the day as basal injections.

Unfortunately, both MDI and insulin pump therapy present problems for patients in implementing basal-bolus therapy. For MDI, certain patients are unlikely or unable to follow the drug regimen required to maintain their medical condition under control. Some patients are squeamish about injecting the drug themselves and others suffer adverse effects from repeated injections, such as bruising at the injection site. Mechanical insulin pens are large and bulky, discouraging the patient from using them regularly. Use of the mechanical insulin pen is also indiscreet.

For insulin pump therapy, delivering fluid continuously and accurately over long periods of time generally requires an electromechanical device to perform and control the pumping. This adds cost and size to the insulin pump due to the pumping actuator itself as well as the required battery and electronics. Many patients are unwilling or unable to use dedicated electronic insulin pumps due to the expense, complication, and obtrusiveness.

It would be desirable to have a mechanical injection pump and method of use that would overcome the above disadvantages.

SUMMARY OF THE INVENTION

One aspect of the invention provides a mechanical injection pump wearable by a user to deliver a first fluid and a second fluid, the mechanical injection pump including: a pump body defining a first fluid chamber and a second fluid chamber, the first fluid chamber being operable to hold the first fluid and the second fluid chamber being operable to hold the second fluid; a common connector having a first inlet, a second inlet, and a common outlet; a first fluid system including the first fluid chamber, a first button drive operably connected to the first fluid chamber, and a first fluid delivery path in fluid communication between the first fluid chamber and the first inlet; and a second fluid system including the second fluid chamber, a second button drive operably connected to the second fluid chamber, and a second fluid delivery path in fluid communication between the second fluid chamber and the second inlet. Force by the user on the first button drive is converted to increased pressure within the first fluid chamber to drive a predetermined volume of the first fluid from the first fluid chamber, through the first fluid delivery path to the common connector, and out the common outlet. Force by the user on the second button drive is converted to increased pressure within the second fluid chamber to drive a predetermined volume of the second fluid from the second fluid chamber, through the second fluid delivery path to the common connector, and out the common outlet.

Another aspect of the invention provides a method of use for a mechanical injection pump, the method including: deploying the mechanical injection pump at the user, the mechanical injection pump having a first fluid system and a second fluid system, the first fluid system including a first fluid chamber, a first button drive operably connected to the first fluid chamber, and a first fluid delivery path in fluid communication between the first fluid chamber and a common outlet, and the second fluid system including a second fluid chamber, a second button drive operably connected to the second fluid chamber, and a second fluid delivery path in fluid communication between the second fluid chamber and the common outlet; applying force to the first button drive to pressurize the first fluid chamber and drive a predetermined volume of the first fluid from the first fluid chamber and out the common outlet; and applying force to the second button drive to pressurize the second fluid chamber and drive a predetermined volume of the first fluid from the second fluid chamber and out the common outlet.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

BRIEF DESCRIPTION OF THE DRAWINGS

FIGS. 3A & 3B are schematic diagrams of a button drive for use with a mechanical injection pump as illustrated in FIG. 2.

FIGS. 4A-4C are schematic diagrams of another button drive for use with a mechanical injection pump of FIG. 2.

FIG. 5 is a schematic diagram of another embodiment of a mechanical injection pump made in accordance with the invention.

FIGS. 6A & 6B are schematic diagrams of a button drive for use with a mechanical injection pump of FIG. 5.

Like elements share like reference numbers in the various drawings.

DETAILED DESCRIPTION

Figure 1:
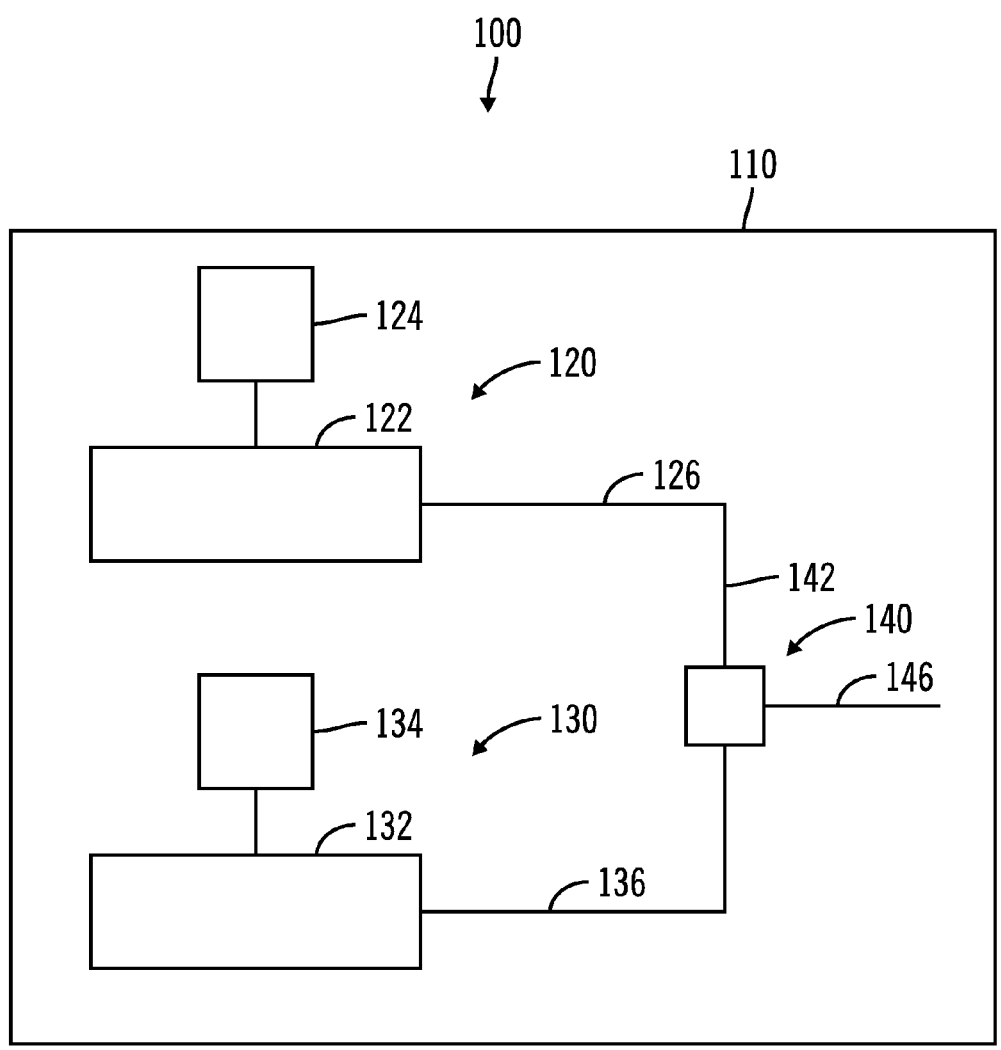
FIG. 1 is a block diagram of a mechanical injection pump made in accordance with the invention.

FIG. 1 is a block diagram of a mechanical injection pump made in accordance with the invention. The mechanical injection pump can be used to deliver a first fluid and a second fluid to a single injection site. In one example, the first fluid can be basal insulin and the second fluid can be bolus insulin. The mechanical injection pump as defined herein can be any injection pump relying on mechanical assemblies to deliver the fluid without electricity. The mechanism used to drive fluid from the fluid chamber is strictly mechanical, and not electrical or electromechanical.

The mechanical injection pump 100 for a user to deliver a first fluid and a second fluid includes a pump body 110, a first fluid system 120, a second fluid system 130, and a common connector 140. The pump body 110 defines a first fluid chamber 122 and a second fluid chamber 132, with the first fluid chamber 122 being operable to hold the first fluid and the second fluid chamber 132 being operable to hold the second fluid. The common connector 140 has a first inlet 142, a second inlet 144, and a common outlet 146. The first fluid system 120 includes the first fluid chamber 122, a first button drive 124 operably connected to the first fluid chamber 122, and first fluid delivery path 126 in fluid communication between the first fluid chamber 122 and the first inlet 142. The second fluid system 130 includes the second fluid chamber 132, a second button drive 134 operably connected to the second fluid chamber 132, and second fluid delivery path 136 in fluid communication between the second fluid chamber 132 and the second inlet 144. In one embodiment, the fluid chamber can include a liner or a bladder to isolate the fluid and on which the button drive can act.

Force applied to one of the button drives delivers a predetermined volume of the selected fluid to the user. Force by the user on the first button drive 124 is converted to increased pressure within the first fluid chamber 122 to drive a predetermined volume of the first fluid from the first fluid chamber 122, through the first fluid delivery path 126 to the common connector 140, and out the common outlet 146. Force by the user on the second button drive 134 is converted to increased pressure within the second fluid chamber 132 to drive a predetermined volume of the second fluid from the second fluid chamber 132, through the second fluid delivery path 136 to the common connector 140, and out the common outlet 146.

The user can also receive force feedback through the button drive. In one embodiment, force feedback to the user can be used to indicate that the button drive has reached the end of travel in the fluid chamber or that the fluid path is occluded. For example, the user can feel increased resistance on the button drive when a piston slideably disposed in the fluid chamber reaches the wall of the fluid chamber indicating end of travel for the piston or when a flow occlusion impedes fluid flow and increases pressure within the fluid chamber.

Those skilled in the art will appreciate that the fluid paths between the fluid chambers and the common outlet can be constructed as desired for a particular application. In one example, the first fluid delivery path 126 and the first inlet 142 are a single piece of tubing. In another example, the common connector 140 is the junction between the first inlet 142, second inlet 144, and common outlet 146, and not a separate component. In yet another example, the first fluid delivery path 126, first inlet 142, second fluid delivery path 136, second inlet 144, common connector 140, and common outlet 146 are a single integral part.

In one example, the mechanical injection pump 100 is used to treat diabetes and the first fluid is basal insulin and the second fluid is bolus insulin. In one example, the predetermined volume delivered per each push of the button drive can be 100-500 µL for basal insulin and 10-50 µL for bolus insulin. Those skilled in the art will appreciate that the mechanical injection pump can be used to deliver any fluid with or without drugs or therapeutic agents in any predetermined volume as desired for a particular application. The fluid as defined herein can be any liquid including those liquids carrying a therapeutic agent, drug, diagnostic agent, or the like. In one example, the predetermined volume of the first fluid can be different from (i.e., not equal to) the predetermined volume of the second fluid, so that the first fluid and the second fluid are administered in different predetermined volumes per push of the respective button drive.

The mechanical injection pump 100 is wearable by the user so that the user can self-administer the first fluid and/or the second fluid as required. In one example, the mechanical injection pump includes an adhesive patch attached to the pump body and the adhesive patch can affix the pump body to the user. The common outlet 146 can have a cannula or hollow needle attached to the pump body, so that the mechanical injection pump is a stand-alone unit and the infusion site is at the mechanical injection pump, or the common outlet 146 can be attached to tubing which carries the fluid to an infusion set with a cannula or hollow needle, so that the infusion site is away from the mechanical injection pump. In another example, the user wears the mechanical injection pump in a purse, holster, or the like, and the common outlet 146 is attached to tubing which carries the fluid to an infusion set with a cannula or hollow needle, so that the infusion site is away from the mechanical injection pump.

Figure 2A:
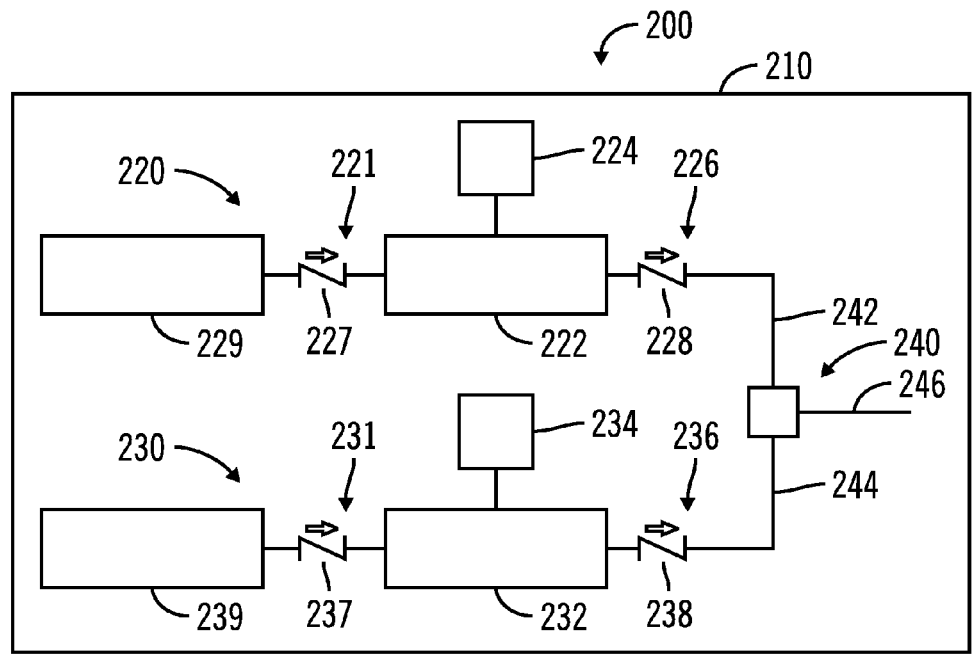
FIGS. 2A & 2B are block and schematic diagrams, respectively, of one embodiment of a mechanical injection pump made in accordance with the invention.
Figure 2B:
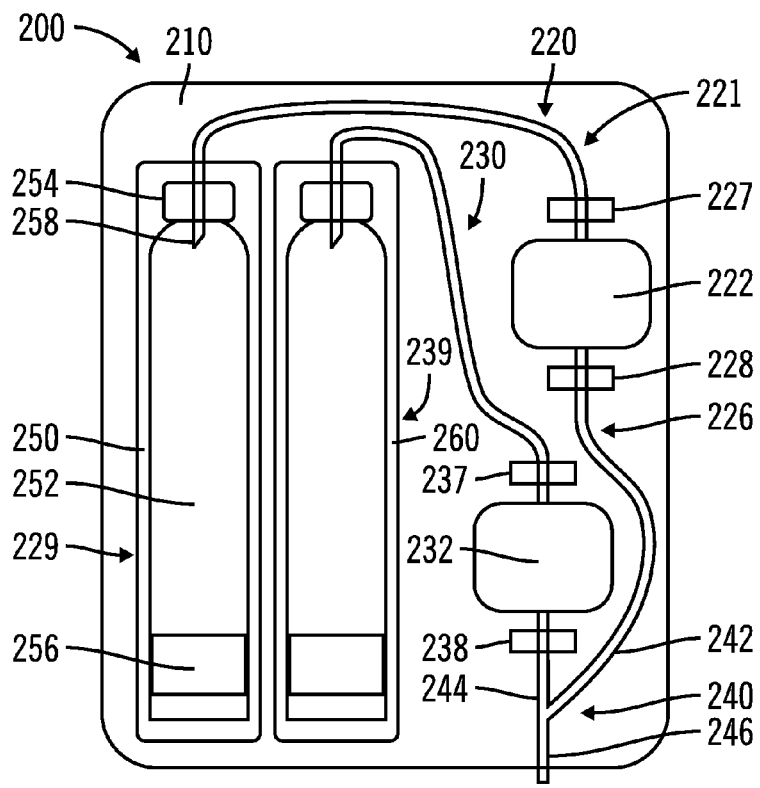

FIGS. 2A & 2B are block and schematic diagrams, respectively, of one embodiment of a mechanical injection pump made in accordance with the invention. In this embodiment, the button drive applies pressure directly to the fluid chamber, which receives the fluid from a fluid reservoir.

The mechanical injection pump 200 for a user to deliver a first fluid and a second fluid includes a pump body 210, a first fluid system 220, a second fluid system 230, and a common connector 240. The pump body 220 defines a first fluid reservoir 229, a first fluid chamber 222, a second fluid reservoir 239, and a second fluid chamber 232. In one embodiment, the portion of the pump body 210 adjacent the first fluid reservoir 229 and/or the second fluid reservoir 239 is transparent so the user can tell when the fluid reservoir needs to be refilled when the fluid reservoirs are refillable, the fluid reservoir needs to be replaced when the fluid reservoirs are replaceable units, or the mechanical injection pump needs to be replaced when the whole mechanical injection pump is disposable. The common connector 240 has a first inlet 242, a second inlet 244, and a common outlet 246.

The first fluid system 220 handling the first fluid includes the first fluid reservoir 229, first inlet check valve 227 in the first fluid supply path 221, first fluid chamber 222, first button drive 224 operably connected to the first fluid chamber 222, and first outlet check valve 228 in the first fluid delivery path 226. The second fluid system 230 handling the second fluid includes the second fluid reservoir 239, second inlet check valve 237 in the second fluid supply path 231, second fluid chamber 232, second button drive 234 operably connected to the second fluid chamber 232, and second outlet check valve 238 in the second fluid delivery path 236.

The check valves control the flow from the fluid reservoir and in and out of the fluid chambers. When the first button drive 224 is actuated to increase pressure within the first fluid chamber 222, the first inlet check valve 227 prevents flow from the first fluid chamber 222 towards the first fluid reservoir 229, and the first outlet check valve 228 permits flow from the first fluid chamber 222 toward the common outlet 246. When the second button drive 234 is actuated to increase pressure within the second fluid chamber 232, the second inlet check valve 237 prevents flow from the second fluid chamber 232 towards the second fluid reservoir 239, and the second outlet check valve 238 permits flow from the second fluid chamber 232 toward the common outlet 246.

With normal pressure within the first fluid chamber 222, i.e., when the first button drive 224 is not actuated, the first inlet check valve 227 permits flow from the first fluid reservoir 229 towards the first fluid chamber 222, and the first outlet check valve 228 prevents flow from the common outlet 246 toward the first fluid chamber 222. With normal pressure within the second fluid chamber 232, i.e., when the second button drive 234 is not actuated, the second inlet check valve 237 permits flow from the second fluid reservoir 239 towards the second fluid chamber 232, and the second outlet check valve 238 prevents flow from the common outlet 246 toward the second fluid chamber 232.

In one embodiment, the size of the fluid chambers can be selected so that the fluid chambers are the predetermined volume of the fluid delivered by the mechanical injection pump, i.e., actuation of the button drive empties the fluid chamber. The volume of the first fluid chamber can equal the predetermined volume of the first fluid and/or the volume of the second fluid chamber can equal the predetermined volume of the second fluid chamber. The volume of the first fluid chamber can be different than (i.e., not equal to) the volume of the second fluid chamber, so that actuation of the first button drive 224 empties the first fluid chamber 222 to deliver one predetermined volume of the first fluid and actuation of the second button drive 234 empties the second fluid chamber 232 to deliver a different predetermined volume of the second fluid.

The fluid reservoirs can be refillable or use pre-filled replaceable units, or the whole mechanical injection pump can be disposable with the fluid reservoirs pre-filled. Referring to FIG. 2B, in one embodiment the pump body defines a first reservoir space 250 and a second reservoir space 260, the first fluid reservoir 229 being removably disposed in the first reservoir space 250 and the second fluid reservoir 232 being removably disposed in the second reservoir space 260. In one example, the replaceable fluid reservoirs can be shaped or keyed so that the first fluid reservoir cannot be interchanged with the second fluid reservoir to preclude administering the first fluid in the second flow path or administering the second fluid in the first flow path. The first reservoir space 250 is complementary in shape to the first fluid reservoir 229, the second reservoir space 260 is complementary in shape to the second fluid reservoir 239, and the shape of the first reservoir space 250 is different than the shape of the second reservoir space 260, so the first fluid reservoir 229 cannot seat in the second reservoir space 260 and the second fluid reservoir 239 cannot seat in the first reservoir space 250. In one example, the first fluid reservoir 229 can be filled with basal insulin and the second fluid reservoir 239 can be filled with bolus insulin.

Referring to FIG. 2B, in one embodiment the replaceable first fluid reservoir 229 can include a hollow body 252, a septum 254 closing one end of the hollow body 252, a slideable piston 256 disposed within the hollow body 252, and insulin disposed within the hollow body 252 between the septum 254 and the slideable piston 256. The first fluid supply path 220 can include a hollow needle 258 projecting into the first reservoir space 250, the hollow needle 258 being operable to pierce the septum 254 and establish fluid communication between the first fluid reservoir 229 and the first fluid chamber 222 when the first fluid reservoir 229 is inserted in the first reservoir space 250. The second fluid reservoir 239 can be similar to the replaceable first fluid reservoir 229. In another embodiment, the insulin is disposed within a bladder, such that the replaceable fluid reservoir is a fluid-filled collapsible bladder.

FIGS. 3A & 3B are schematic diagrams of a button drive for use with a mechanical injection pump as illustrated in FIG. 2. In this example, the button of the button drive applies pressure to the fluid in the fluid chamber.

Referring to FIG. 3A, the button drive 324 includes a piston 362 slideably disposed in the fluid chamber 322 and a spring 364 biasing the piston 362 toward the released position shown in FIG. 3A. Referring to FIG. 3B, the force (indicated by arrow 366) on the piston 362 by the user slides the piston 362 to the compressed position shown in FIG. 3B to drive the predetermined volume of the first fluid from the first fluid chamber. The inlet check valve 327 prevents flow from the fluid chamber 322 towards the fluid reservoir and the outlet check valve 328 permits flow from the fluid chamber 322 toward the common outlet. When the force on the piston 362 by the user is removed, the spring 364 slides the piston 362 from the compressed position to the released position to refill the fluid chamber 322, with the inlet check valve 327 permitting flow from the fluid reservoir to the fluid chamber 322 and the outlet check valve 328 preventing flow from the fluid chamber 322 toward the common outlet. The button drive 324 can be used as the first button drive 224 and/or the second button drive 234 shown in FIGS. 2A & 2B.

FIGS. 4A-4C are schematic diagrams of another button drive for use with a mechanical injection pump of FIG. 2. In this example, the button of the button drive compresses a spring, which applies pressure to the fluid in the fluid chamber when the button is released.

Referring to FIG. 4A, the button drive 424 includes a piston 462 slideably disposed in the fluid chamber 422 and a spring 464 biasing the piston 462 toward the released position shown in FIG. 4A. In this example, a button 460 is operably connected to the piston 462. Referring to FIG. 4B, the force (indicated by arrow 466) on the piston 462 by the user slides the piston 462 to the compressed position shown in FIG. 4B to fill the fluid chamber 422 with the predetermined volume of the fluid from the fluid chamber 422. The inlet check valve 427 permits flow from the fluid reservoir to the fluid chamber 422 and the outlet check valve 428 prevents flow from the fluid chamber 422 toward the common outlet. Referring to FIG. 4C, which illustrates the piston 462 at an intermediate position between the compressed position and the released position, release of the force on the piston 462 by the user slides the piston 462 to the released configuration to drive the predetermined volume of the fluid from the fluid chamber. The inlet check valve 427 prevents flow from the fluid chamber 422 towards the fluid reservoir and the outlet check valve 428 permits flow from the fluid chamber 422 toward the common outlet. The button drive 424 can be used as the first button drive 224 and/or the second button drive 234 shown in FIGS. 2A & 2B.

FIG. 5 is a schematic diagram of another embodiment of a mechanical injection pump made in accordance with the invention. In this embodiment, the button drive advances a piston in the fluid chamber to apply pressure to the fluid.

The mechanical injection pump 500 for a user to deliver a first fluid and a second fluid includes a pump body 510, a first fluid system 520, a second fluid system 530, and a common connector 540. The pump body 520 defines a first fluid chamber 522 and a second fluid chamber 532. In one embodiment, portion of the pump body 510 adjacent the first fluid reservoir 529 and/or the second fluid reservoir 539 is transparent so the user can tell when the fluid reservoir needs to be refilled when the fluid reservoirs are refillable, the fluid reservoir needs to be replaced when the fluid reservoirs are replaceable units, or the mechanical injection pump needs to be replaced when the whole mechanical injection pump is disposable. The common connector 540 has a first inlet 542, a second inlet 544, and a common outlet 546.

The first fluid system 520 handling the first fluid includes the first fluid chamber 522, first button drive 524, first piston 527 slideably disposed in the first fluid chamber 522, first axial shaft 529 operably connected between the first button drive 524 and the first piston 527, and first fluid delivery path 526 in fluid communication between the first fluid chamber 522 and the first inlet 542. The first fluid system 520 can optionally include a first outlet check valve 528 to prevent flow from the common connector 540 toward the first fluid chamber 522. The second fluid system 530 handling the second fluid includes the second fluid chamber 532, second button drive 534, second piston 537 slideably disposed in the second fluid chamber 532, second axial shaft 539 operably connected between the second button drive 534 and the second piston 537, and second fluid delivery path 536 in fluid communication between the second fluid chamber 532 and the second inlet 542. The second fluid system 530 can optionally include a second outlet check valve 538 to prevent flow from the common connector 540 toward the second fluid chamber 532.

The user pushes the button drive to advance the piston and deliver the predetermined volume of fluid. The force by the user on the first button drive 534 advances the first piston 537 a first predetermined distance into the first fluid chamber 532 to drive the predetermined volume of the first fluid out the common outlet 546. The force by the user on the second button drive 534 advances the second piston 537 a second predetermined distance into the second fluid chamber 532 to drive the predetermined volume of the second fluid out the common outlet 546. Those skilled in the art will appreciate that the cross sections of and/or predetermined distances for the first fluid chamber 532 and the second fluid chamber 532 can be selected as desired for a particular application to deliver the desired predetermined volume of the first fluid and second fluid. The predetermined volumes of the first fluid and second fluid can be the same or can be different.

FIGS. 6A & 6B are schematic diagrams of a button drive for use with a mechanical injection pump of FIG. 5. In this example, the button drive is a ratchet and pawl mechanism.

Referring to FIGS. 6A & 6B, the button drive 624 includes an axially fixed ratchet wheel 640 and a ratchet assembly 650. The axially fixed ratchet wheel 640 has exterior teeth 642 and internal threads 644. The axial shaft 629 has external threads 631, which are engaged with the internal threads 646 of the axially fixed ratchet wheel 640. The ratchet assembly 650 is operable to engage the exterior teeth 644 of the axially fixed ratchet wheel 640 and rotate the axially fixed ratchet wheel 640 a predetermined angle in response to the force (illustrated by arrow 670) by the user on the button drive 624. The axially fixed ratchet wheel 640 is fixed in axial position relative to the fluid chamber 622, so rotation of the axially fixed ratchet wheel 640 advances the piston 627 within the fluid chamber 622 the predetermined distance into the fluid chamber 622 to drive the predetermined volume of the fluid out the common outlet.

In this example, the ratchet assembly 650 includes an arm 652 having a pivot end 653 and a swing end 654, a pivot end pawl 656 pivotally attached at the pivot end 653, a swing end pawl 658 pivotally attached at the swing end 654, and a spring 659 biasing the swing end 654 in the direction opposite the force illustrated by the arrow 670. The swing end pawl 658 and the pivot end pawl 656 are biased toward and ride along the teeth 644 of the axially fixed ratchet wheel 640. When the user applies force as indicated by arrow 670, the arm 652 rotates about the swing end 654. The swing end pawl 658 rotates the axially fixed ratchet wheel 640 one tooth forward as indicated by arrow 680. The pivot end pawl 656 follows the axially fixed ratchet wheel 640 one tooth forward to keep the axially fixed ratchet wheel 640 from counter-rotating when the force indicated by arrow 670 is removed and the spring 659 counter-rotates the arm 652 about the swing end 654.

Those skilled in the art will appreciate that the button drive in this example can be any mechanical assembly operable to convert force on a button by the user to axial motion of the axial shaft and the piston. In another example, the axial shaft has external serrations and a linear ratchet engaging the external serrations advances the axial shaft and the piston in the manner of the mechanism used in ratchet rod caulk guns. In other examples, the mechanical assembly can be a mechanical assembly similar to the mechanical assembly used in injection pens, such as the NovoLog® FlexPen® pre-filled, disposable insulin pen from Novo Nordisk A/S of Bagsvaerd, Denmark, the Humalog® Kwik-Pen® lispro insulin disposable delivery device from Eli Lilly, Inc., of Indianapolis, Ind., or the like. The mechanical assembly includes a setting knob which can be used to arm the pen for injection. Turning the setting knob turns an operating plunger, which is supported in the pen housing by a helical thread of substantial pitch. The operating plunger turned by the setting knob advances the operating plunger longitudinally relative to the pen housing, extending the operating plunger from the pen housing until a desired injection volume is indicated. The user then pushes the back of the operating plunger and the mechanical assembly moves a syringe piston coupled to the operating plunger an accurately scaled distance to deliver the desired injection volume. The mechanical assembly can also include a dose selector knob to allow for adjustable delivery volumes.

Figure 7:
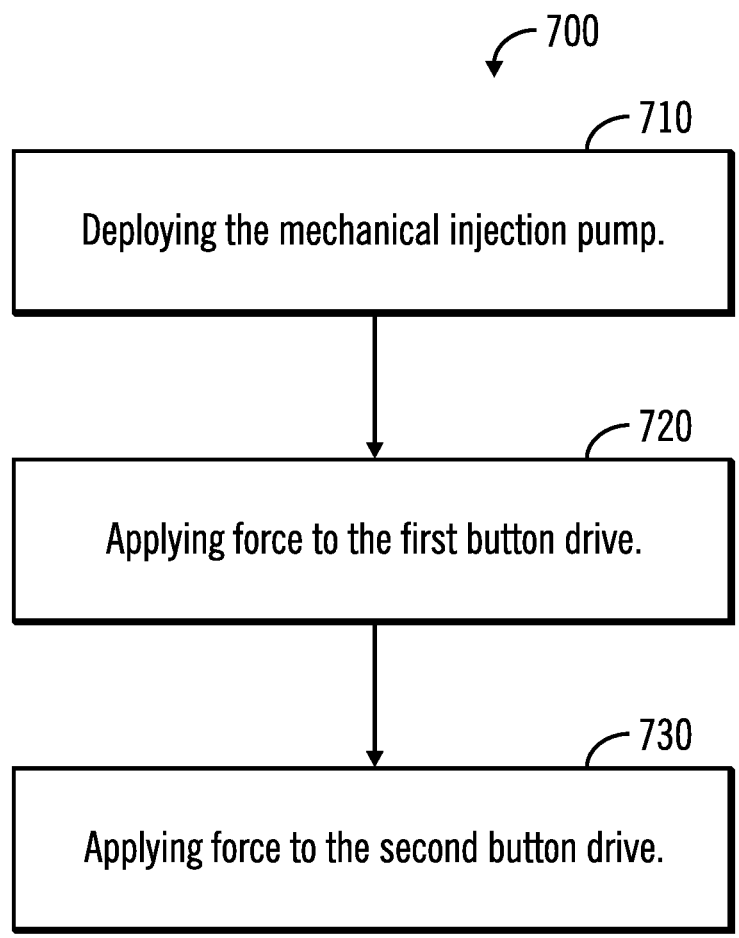
FIG. 7 is a flow chart of a method of use for a mechanical injection pump in accordance with the invention.

FIG. 7 is a flow chart of a method of use for a mechanical injection pump in accordance with the invention. The method 700 can be used with mechanical injection pumps as described in conjunction with FIGS. 1, 2, 5 as described above, or the like.

Referring to FIG. 7, the method 700 includes deploying the mechanical injection pump 710 at the user, the mechanical injection pump having a first fluid system and a second fluid system, the first fluid system including a first fluid chamber, a first button drive operably connected to the first fluid chamber, and a first fluid delivery path in fluid communication between the first fluid chamber and a common outlet, and the second fluid system including a second fluid chamber, a second button drive operably connected to the second fluid chamber, and a second fluid delivery path in fluid communication between the second fluid chamber and the common outlet; applying force to the first button drive 720 to pressurize the first fluid chamber and drive a predetermined volume of the first fluid from the first fluid chamber and out the common outlet; and applying force to the second button drive 730 to pressurize the second fluid chamber and drive a predetermined volume of the first fluid from the second fluid chamber and out the common outlet.

The method 700 can be used with a mechanical injection pump that is a stand-alone unit at the infusion site or that is away from the infusion site. In one embodiment, the mechanical injection pump for use in the method 700 includes an adhesive patch and the common outlet is a cannula. The deploying 710 further includes inserting the cannula subcutaneously in the user and affixing the mechanical injection pump to the user with the adhesive patch at the infusion site. In one embodiment, the method 700 uses an infusion set having an adhesive patch and a cannula. The deploying 710 further includes inserting the cannula subcutaneously in the user, affixing the infusion set to the user with the adhesive patch at the infusion site, and connecting tubing between the common outlet and the cannula to place the common outlet and the cannula in fluid communication.

In one embodiment of the method 700 for treating diabetes, the first fluid is basal insulin and the second fluid is bolus insulin. The applying force to the first button drive 720 further includes applying force to the first button drive intermittently when the user is fasting to deliver the basal insulin, and the applying force to the second button drive 730 further includes applying force to the second button drive at mealtimes of the user to deliver the bolus insulin. In one example, the basal insulin can be delivered in a predetermined volume of 100-500 µL per each push of the first button drive and can be delivered once every 24 hours. In one example, the bolus insulin can be delivered in a predetermined volume of 10-50 µL per each push of the second button drive at mealtimes. Those skilled in the art will appreciate that the predetermined volumes can be selected as desired for a particular dosage as required for a particular user.

It is important to note that FIGS. 1-7 illustrate specific applications and embodiments of the invention, and are not intended to limit the scope of the present disclosure or claims to that which is presented therein. Upon reading the specification and reviewing the drawings hereof, it will become immediately obvious to those skilled in the art that myriad other embodiments of the invention are possible, and that such embodiments are contemplated and fall within the scope of the presently claimed invention.

For example, the mechanical injection pump having two fluid systems can be used so that only one of the two fluid systems is filled and used to deliver a single fluid. In another example, the mechanical injection pump can have a single fluid system. The mechanical injection pump can be wearable by a user to deliver a fluid, and the mechanical injection pump can include: a pump body defining a fluid chamber operable to hold the fluid; and a fluid system including the fluid chamber, a button drive operably connected to the fluid chamber, and a fluid delivery path in fluid communication between the fluid chamber and a pump outlet; wherein force by the user on the button drive is converted to increased pressure within the fluid chamber to drive a predetermined volume of the fluid from the fluid chamber, through the fluid delivery path to the common connector, and out the pump outlet. In yet another example, the mechanical injection pump can include components and/or sensors involving electricity, although the mechanism of the button drive used to increase pressure in and drive fluid from the fluid chamber remains strictly mechanical, and is not electrical or electro-mechanical.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

The invention claimed is:

1. A mechanical injection pump wearable by a user to deliver a first fluid and a second fluid, the mechanical injection pump comprising:
   a pump body defining a first fluid chamber and a second fluid chamber, the first fluid chamber being operable to hold the first fluid and the second fluid chamber being operable to hold the second fluid;
   a common connector having a first inlet, a second inlet, and a common outlet;
   a first fluid system including the first fluid chamber, a first button drive operably connected to the first fluid chamber, a first fluid delivery path in fluid communication between the first fluid chamber and the first inlet, a first piston slideably disposed in the first fluid chamber, and a first axial shaft operably connected between the first button drive and the first piston, wherein the first axial shaft has external threads, and the first button drive comprises:
      an axially fixed ratchet wheel having exterior teeth and internal threads, the internal threads being engaged with the first external threads of the first axial shaft; and
      a ratchet assembly operable to engage the exterior teeth of the axially fixed ratchet wheel; and
   a second fluid system including the second fluid chamber, a second button drive operably connected to the second fluid chamber, a second fluid delivery path in fluid communication between the second fluid chamber and the second inlet, a second piston slideably disposed in the second fluid chamber, and a second axial shaft operably connected between the second button drive and the second piston;
   wherein force by the user on the first button drive causes the ratchet assembly to rotate the axially fixed ratchet wheel a predetermined angle to advance the first piston a first predetermined distance into the first fluid chamber to drive a predetermined volume of the first fluid from the first fluid chamber, through the first fluid delivery path to the common connector, and out the common outlet; and
   force by the user on the second button drive advances the second piston a second predetermined distance into the second fluid chamber to drive a predetermined volume of the second fluid from the second fluid chamber, through the second fluid delivery path to the common connector, and out the common outlet.

2. The mechanical injection pump of claim 1 wherein the first fluid is basal insulin and the second fluid is bolus insulin.

3. The mechanical injection pump of claim 1 wherein the predetermined volume of the first fluid is not equal to the predetermined volume of the second fluid.

4. The mechanical injection pump of claim 1 further comprising an adhesive patch attached to the pump body, the adhesive patch being operable to affix the pump body to the user.

5. The mechanical injection pump of claim 1 wherein volume of the first fluid chamber equals the predetermined volume of the first fluid and volume of the second fluid chamber equals the predetermined volume of the second fluid chamber.

6. The mechanical injection pump of claim 5 wherein the volume of the first fluid chamber is not equal to the volume of the second fluid chamber.

7. The mechanical injection pump of claim 1 for use with a first fluid reservoir and a second fluid reservoir, wherein the pump body further defines a first reservoir space and a second reservoir space, the first fluid reservoir being removably disposed in the first reservoir space and the second fluid reservoir being removably disposed in the second reservoir space.

8. The mechanical injection pump of claim 7 wherein the first reservoir space is complementary in shape to the first fluid reservoir, the second reservoir space is complementary in shape to the second fluid reservoir, and the shape of the first reservoir space is different than the shape of the second reservoir space, so the first fluid reservoir cannot seat in the second reservoir space and the second fluid reservoir cannot seat in the first reservoir space.

9. The mechanical injection pump of claim 7 wherein:
the first fluid reservoir comprises:
  a hollow body;
  a septum closing one end of the hollow body;
  a slideable piston disposed within the hollow body; and
  insulin disposed within the hollow body between the septum and the slideable piston; and
the first fluid supply path further comprises a hollow needle projecting into the first reservoir space, the hollow needle being operable to pierce the septum and establish fluid communication between the first fluid reservoir and the first fluid chamber when the first fluid reservoir is inserted in the first reservoir space.

10. The mechanical injection pump of claim 1 for use with a first fluid reservoir and a second fluid reservoir wherein a portion of the pump body adjacent the first fluid reservoir and the second fluid reservoir is transparent.

11. A method of use for a mechanical injection pump, the method comprising:
deploying the mechanical injection pump at the user, the mechanical injection pump having a first fluid system and a second fluid system,
the first fluid system including a first fluid chamber, a first button drive operably connected to the first fluid chamber, a first fluid delivery path in fluid communication between the first fluid chamber and a common outlet, a first piston slideably disposed in the first fluid chamber, and a first axial shaft operably connected between the first button drive and the first piston, wherein the first axial shaft has external threads, and the first button drive comprises:
  an axially fixed ratchet wheel having exterior teeth and internal threads, the internal threads being engaged with the first external threads of the first axial shaft; and
  a ratchet assembly operable to engage the exterior teeth of the axially fixed ratchet wheel, and
the second fluid system including a second fluid chamber, a second button drive operably connected to the second fluid chamber, a second fluid delivery path in fluid communication between the second fluid chamber and the common outlet, a second piston slideably disposed in the second fluid chamber, and a second axial shaft operably connected between the second button drive and the second piston;
applying force to the first button drive to cause the ratchet assembly to rotate the axially fixed ratchet wheel a predetermined angle to advance the first piston a first predetermined distance into the first fluid chamber and drive a predetermined volume of the first fluid from the first fluid chamber and out the common outlet; and
applying force to the second button drive to advance the second piston a second predetermined distance into the second fluid chamber and drive a predetermined volume of the first fluid from the second fluid chamber and out the common outlet.

12. The method of claim 11 wherein the mechanical injection pump includes an adhesive patch and the common outlet is a cannula, and the deploying further comprises inserting the cannula subcutaneously in the user and affixing the mechanical injection pump to the user with the adhesive patch.

13. The method of claim 11 for use with an infusion set having an adhesive patch and a cannula, the deploying further comprising inserting the cannula subcutaneously in the user, affixing the infusion set pump to the user with the adhesive patch, and connecting tubing between the common outlet and the cannula to place the common outlet and the cannula in fluid communication.

14. The method of claim 11 wherein the first fluid is basal insulin and the second fluid is bolus insulin, the applying force to the first button drive further comprises applying force to the first button drive intermittently when the user is fasting to deliver the basal insulin, and the applying force to the second button drive further comprises applying force to the second button drive at mealtimes of the user to deliver the bolus insulin.

* * * * *